United States Patent [19]
Raymond

[11] Patent Number: 5,673,588
[45] Date of Patent: Oct. 7, 1997

[54] INFUSION PUMP RETRACTION MECHANISM

[75] Inventor: Jeffrey A. Raymond, North Andover, Mass.

[73] Assignee: Abbott Laboratories, Abbott Park, Ill.

[21] Appl. No.: 378,787

[22] Filed: Jan. 26, 1995

[51] Int. Cl.⁶ .................................................. F16H 25/18
[52] U.S. Cl. ............................ 74/106; 74/100.1; 74/36; 200/400
[58] Field of Search .................... 74/102, 106, 100.1, 74/36, 520; 604/151; 200/400, 401

[56] References Cited

U.S. PATENT DOCUMENTS

| | | | |
|---|---|---|---|
| D. 290,656 | 6/1987 | Kaleskas | D24/53 |
| 647,144 | 4/1900 | Mercer | 74/106 |
| 872,885 | 12/1907 | Anderson | 74/106 |
| 1,525,989 | 2/1925 | Hill | 74/106 |
| 2,995,043 | 8/1961 | Lusk | 74/106 |
| 3,187,593 | 6/1965 | McCloud | 74/106 |
| 3,582,591 | 6/1971 | Few | 200/400 |
| 4,696,671 | 9/1987 | Epstein et al. | 604/67 |
| 4,753,270 | 6/1988 | Lawhite et al. | 137/624.18 |
| 4,828,545 | 5/1989 | Epstein et al. | 604/66 |
| 4,865,584 | 9/1989 | Epstein et al. | 604/67 |
| 5,100,380 | 3/1992 | Epstein et al. | 604/67 |
| 5,108,367 | 4/1992 | Epstein et al. | 604/67 |
| 5,127,907 | 7/1992 | Coutré et al. | 604/151 |
| 5,153,827 | 10/1992 | Coutré et al. | 364/413.02 |
| 5,304,126 | 4/1994 | Epstein et al. | 904/67 |
| 5,317,506 | 5/1994 | Coutré et al. | 364/413.02 |
| 5,426,990 | 6/1995 | Francart | 74/100.1 |
| 5,545,867 | 8/1996 | Castonguay | 200/400 |

*Primary Examiner*—Khoi Q. Ta
*Assistant Examiner*—David M. Fenstermacher
*Attorney, Agent, or Firm*—Neal D. Marcus; Beverly E. Hjorth

[57] ABSTRACT

A retraction mechanism is disclosed for retracting and engaging the pumping mechanism assembly of an infusion pump with an infusate flow path. The retraction mechanism provides a linkage which converts rotary motion of a handle about an axis to linear motion along a line parallel to the axis. The linkage is connected to the pumping mechanism assembly to cause the pumping mechanism assembly to retract from or engage with the flow path via a disposable cassette. The retraction mechanism is biassed toward the engaged position to prevent free flow of infusates on the flow path. The retraction mechanism is operable in two steps: first, the handle is pulled out against the biassing force; second, the handle is rotated until it locks into the retracted position. The mechanism includes a toggle linkage which aids in locking the mechanism in the retracted position and in biassing the mechanism to the engaged position when the handle is moved out of the locked retraction position.

29 Claims, 8 Drawing Sheets

INFUSION PUMP RETRACTION MECHANISM

FIELD OF THE INVENTION

This invention relates to medical devices and more particularly to infusion pumps.

BACKGROUND OF THE INVENTION

Infusion systems are used to administer one or more infusates to patients. Typically, infusion systems incorporate a pumping mechanism assembly which delivers infusates on a flow path at controlled rates and times. In many systems, the flow path past the pumping mechanism assembly is provided as a removable or disposable member, such as a cassette or flexible tubing, which engages the pumping mechanism assembly. An engagement mechanism is used to move the flow path and the pumping mechanism assembly into engagement with each other for infusions and out of engagement for removing the disposable member.

For example, U.S. Pat. No. 4,828,545, discloses an infusion system in which the flow path is provided in a removable cassette which is mounted to the system housing. A flexible membrane in the cassette defines the flow path and pump and valve chambers. The pumping mechanism assembly, including pump and valve pistons, is moved into an engaged position in which the pump and valve pistons can engage the flexible membrane to control entry of infusates into the pump and valve chambers. The engagement of the pumping mechanism assembly also locks the cassette in place and prevents the free flow of infusates on the flow path. To remove the cassette, the pumping mechanism assembly is retracted from the cassette.

A linkage is provided in the system housing to slide the pumping mechanism assembly into engagement with and retraction from the cassette. A handle on the system housing is provided to control movement of the linkage. The handle is rotatable about an axis parallel to the direction of sliding of the pumping mechanism assembly. The handle is also movable along the axis for release from a locked position, in which the pumping mechanism assembly is engaged with the cassette, to an unlocked position, in which the handle may be rotated to retract the pumping mechanism assembly.

SUMMARY OF THE INVENTION

The retraction mechanism for an infusion pump of the present invention provides a linkage which converts rotary motion of a handle about an axis to linear motion along a line parallel to the rotation axis. The mechanism is connected to a pumping mechanism assembly support to cause the pumping mechanism assembly support to retract from or engage with a flow path such as through a cassette. The mechanism is strong, simple, and compact, while also being intuitive to operate.

The retraction mechanism includes a toggle linkage which aids in locking the mechanism in the retracted position and in biassing the mechanism to the engaged position when the handle is moved out of the locked position. The toggle linkage is coupled to a pull rod assembly which includes a linearly movable pull rod fixed to the pumping mechanism assembly support. The pull rod is supported by a bearing surface, which provides a reduced friction, linear motion. The pull rod assembly also includes a support arm which is also fixed to the pumping mechanism assembly support. The support arm provides additional stability to the motion of the pumping mechanism assembly support.

The toggle linkage is coupled at an opposite end to a retraction assembly comprising a retraction shaft having the handle thereon. The shaft is biassed toward the engaged position and retained in the engaged position by a engaged position stop. Maintaining the engaged position aids in preventing unintended free flow of fluid along the flow path by, for example, accidental retraction of the pumping mechanism assembly.

To retract the mechanism, the retraction shaft is first pulled out past the engaged position stop, and then the shaft is rotated until it locks into the retracted position. This two-step operation also aids in preventing accidental retraction of the mechanism. The rotation of the shaft is further limited in both directions by two additional stops, thereby limiting the translation to only the permitted and necessary positions.

The retraction mechanism requires only a minimum of fasteners to attach to the chassis and allows for some adjustment when being assembled to accommodate variations in parts, such as dimensional tolerances.

DESCRIPTION OF THE DRAWINGS

The invention will be more fully understood from the following detailed description taken in conjunction with the accompanying drawings in which.

DETAILED DESCRIPTION OF THE INVENTION

Figure 1:
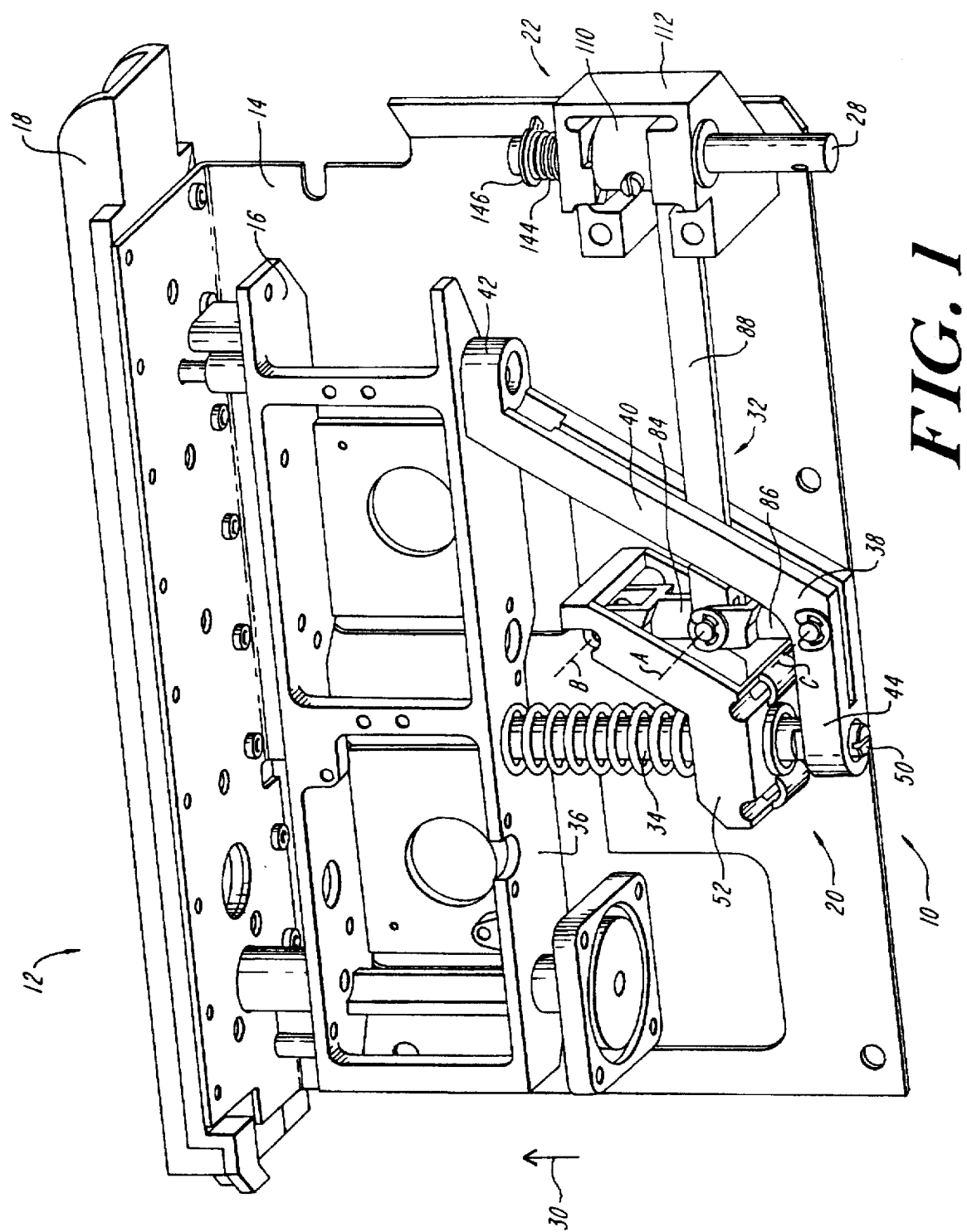
FIG. 1 is an isometric view of the retraction mechanism of the present invention in the retracted position.
Figure 2:
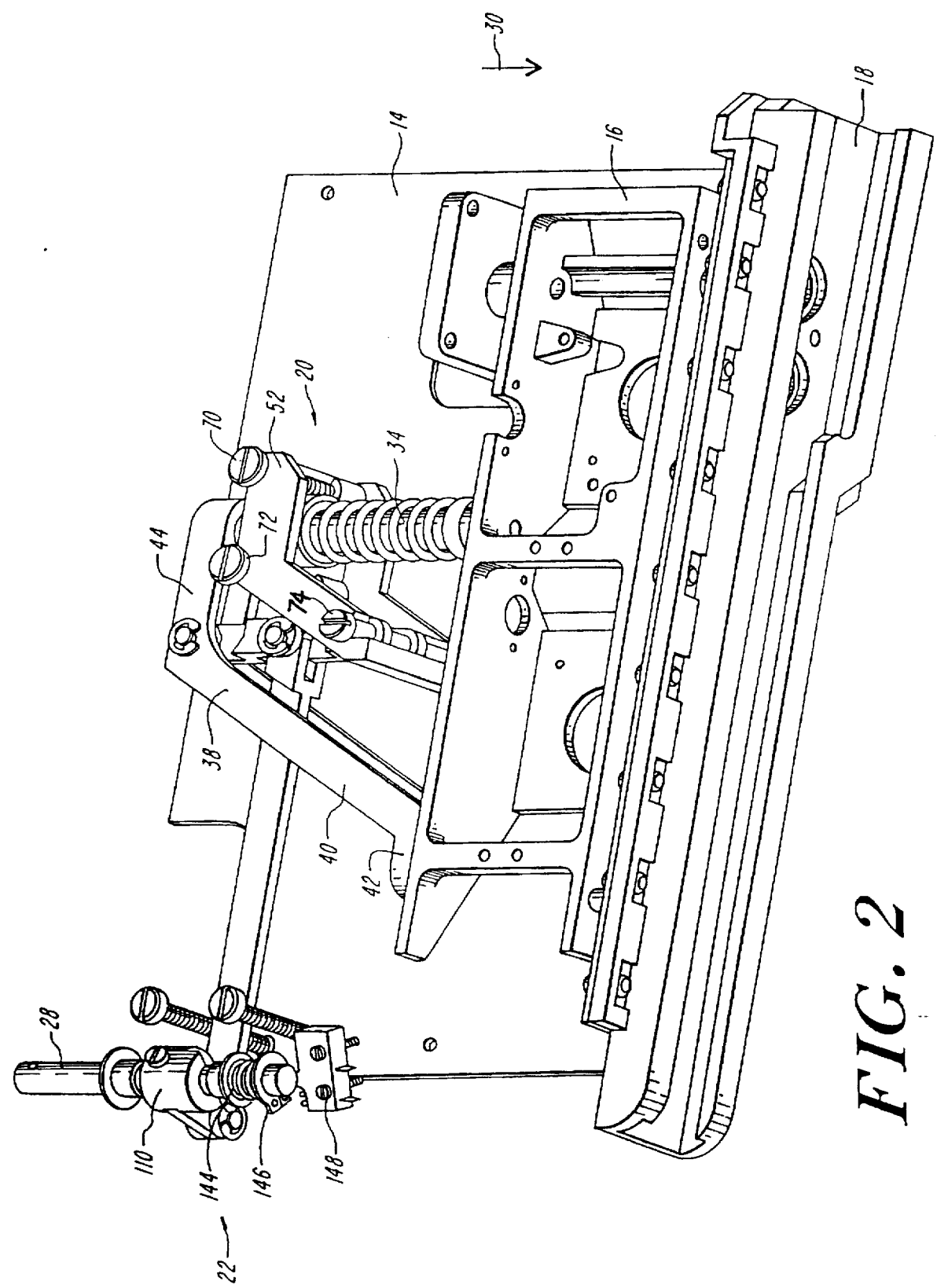
FIG. 2 is a further isometric view of the retraction mechanism of FIG. 1.

The retraction mechanism 10 of the present invention is shown generally in FIGS. 1–5 in conjunction with an infusion system 12 incorporating a removable cassette (not shown). A flow path and pumping and valve chambers are provided in the cassette. The infusion system includes a chassis 14 to which is mounted a pumping mechanism assembly support 16. The pumping mechanism assembly support houses the various elements of the pumping mechanism assembly (not shown), such as the pump and valve pistons. A holster 18, into which the cassette is slid for engagement with the pumping mechanism assembly, is also mounted on the chassis 14.

Figure 6:
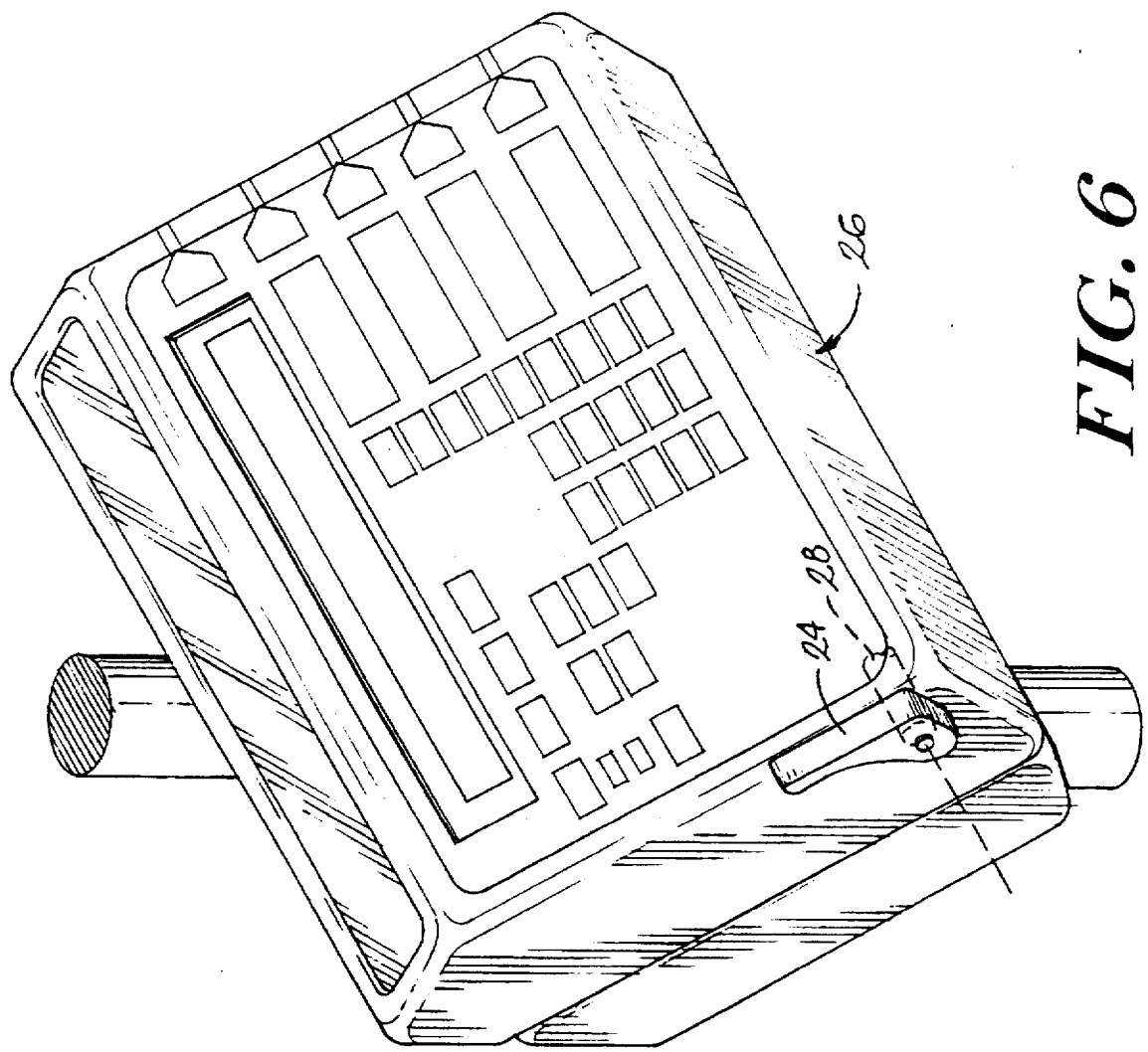
FIG. 6 is a view of an infusion system housing incorporating the retraction mechanism of the present invention.

The retraction mechanism includes a linearly movable pull rod assembly 20, which is fixed to the pumping mechanism assembly support 16, and a retraction assembly 22, which includes a handle 24 extending outside of the infusion system housing 26 (see FIG. 6). The handle 24 is coupled to a shaft 28 which is movable linearly along an axis parallel to the direction of the pull rod assembly motion (indicated by arrow 30) and rotatable about the axis. A toggle linkage 32 interconnects the retraction assembly 22 and the pull rod assembly 20 and converts the rotary motion of the retraction assembly to the linear motion of the pull rod assembly.

The pull rod assembly 20 of the retraction mechanism includes a pull rod 34 which is fastened at a first end to a wall 36 of the pumping mechanism assembly support 16, such as by a screw (not shown). The pull rod assembly also includes a support arm 38 having a main arm 40. The support arm also has a short end piece 42 and a long end piece 44 which extend at an angle from the main arm 40. A slot 46 (see FIGS. 7 and 8) is provided through the main arm 40 and the long end piece 44, discussed further below. The short end piece 42 of the support arm 38 is fastened to the wall 36 of the pumping mechanism assembly support 16, such as by a screw 48 (see FIG. 3). The long end piece 44 of the support arm 38 is fastened to a second end of the pull rod 34, such as by a screw 50. In this manner, the pull rod 34 and the support arm 38 are able to move in tandem in a direction parallel to the axis of the pull rod, indicated by the arrow 30. The pumping mechanism assembly support 16 is also able to move with the pull rod and the support arm in the direction of arrow 30 parallel to the pull rod axis. The support arm 38 provides additional support for the pumping mechanism assembly support 16 and stabilizes the motion thereof. The pull rod 34 and support arm 38 may be fastened to each other and to the pumping mechanism assembly support 16 in any other suitable manner known in the art.

Figure 7:
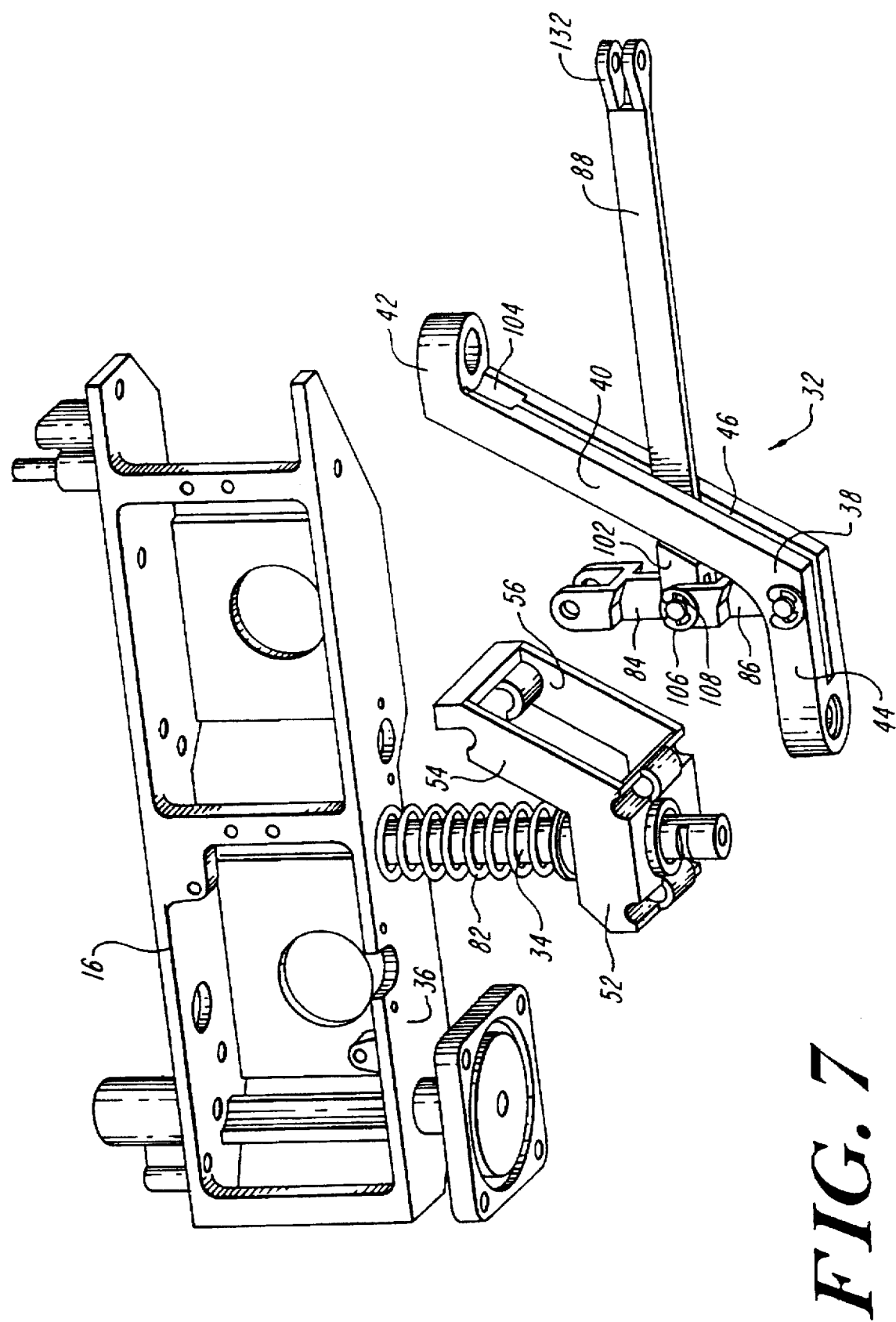
FIG. 7 is an exploded isometric view of part of the retraction mechanism of the present invention.
Figure 8:
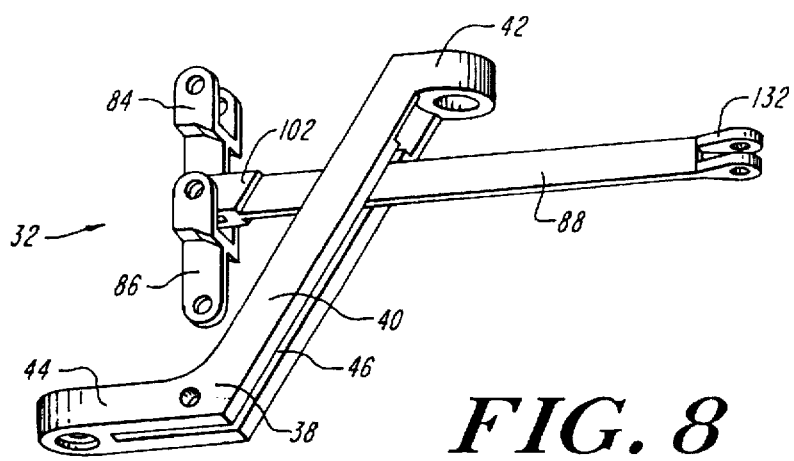
FIG. 8 is an isometric view of the toggle linkage of the present invention.
Figure 9A:
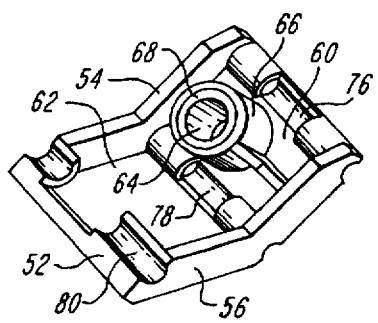
FIGS. 9A and 9B are isometric views of the pull rod brace of the present invention.
Figure 9B:
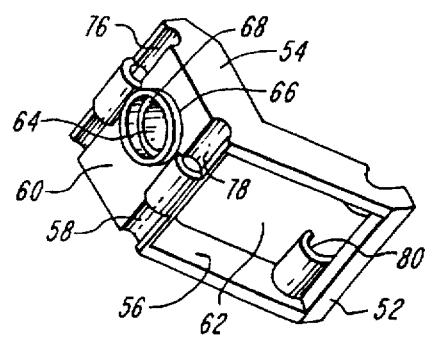

A pull rod brace 52 is mounted to the chassis 14 to support the pull rod 34. The pull rod brace has upper and lower members 54,56 in the form of two legs joined at a corner 58 (see FIGS. 9A and 9B). A wall 60 is formed between the upper and lower members along one leg thereof. The space 62 between the other legs of the upper and lower members is left open, for a purpose to be described further below. An opening 64 defined by a cylindrical collar 66 extending from the wall 60 is formed to accommodate the pull rod 34. The interior surface of the collar 66 is lined by a bearing 68, which may be made from any suitable bearing material, to ease movement of the pull rod 34 therethrough and provide additional support for the pull rod. The pull rod brace 52 is fastened to the chassis 14 by, for example, inserting screws 70,72,74 through openings 76,78,80 at the ends and the corner 58 of the brace. The openings 76,78,80 may be formed as alternating half cylinders, as shown in FIGS. 7, 9A, and 9B, to allow the brace to be more readily molded as a single piece.

A compression spring 82 is provided around the pull rod 34 between the end of the cylindrical collar 66 and the wall 36 of the pump mechanism support 16. The spring 82 biases the pump mechanism support 16 away from the pull rod brace 52, which aids in maintaining the retraction mechanism in the engaged position, described further below. Any other suitable biassing mechanism may be provided.

Figure 10:
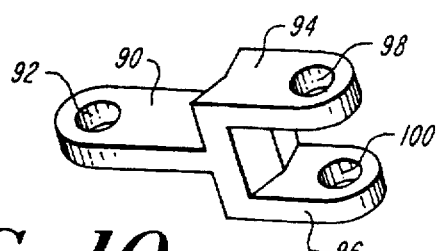
FIG. 10 is an isometric view of a toggle link of the present invention.

The toggle linkage 32 comprising a pair of toggle links 84,86 and a connecting link 88 is rotatably attached to the pull rod brace 52 at the end thereof and to the long end piece 44 of the support arm 38. Preferably, each toggle link is formed identically, as shown in FIG. 10, to reduce the tooling. Referring to FIG. 10, each toggle link has a single arm 90, with a hole 92 formed at the end, and a pair of arms 94,96 forming a fork, also with holes 98,100 formed in alignment at the ends thereof. The connecting link 88 also includes a forked end 102 comprising a pair of arms having aligned holes therethrough.

The connecting link 88 is inserted through the slot 46 in the main arm 40 of the support arm 38. A widened portion 104 of the slot 46 is provided to slip the forked end 102 through during assembly. The single arm 90 of a first 84 of the two toggle links is inserted between the pair of arms of the forked end 102 of the connecting link 88 with the holes aligned. The nested single arm and forked end are further inserted between the pair of arms of the forked end of the second 86 of the two toggle links, also with the holes aligned. A toggle pin 106 is inserted through the aligned holes and held in place by a clip 108 on both ends. The two toggle links 84,86 and the connecting link 88 are, in this manner, rotatably joined about an axis A defined by the aligned holes and the toggle pin 106.

The holes in the pair of arms of the first toggle link 84 are aligned with the opening 80 at the end of the pull rod brace 52, and the first toggle link 84 is fastened to the pull rod brace, as by the screw 74 noted above, for rotation about an axis B defined by the aligned holes and the screw 74. The single arm of the second toggle link 86 is inserted in the slot 46 of the long end piece 44 of the support arm 38. A hole in the long end piece 44 is aligned with the hole in the single arm. A toggle pin 108 is inserted through the holes and fastened with clips. The second toggle link 86 is thereby fastened to the support arm 38 for rotation about an axis C defined by the aligned holes and the toggle pin 108.

Figure 3:
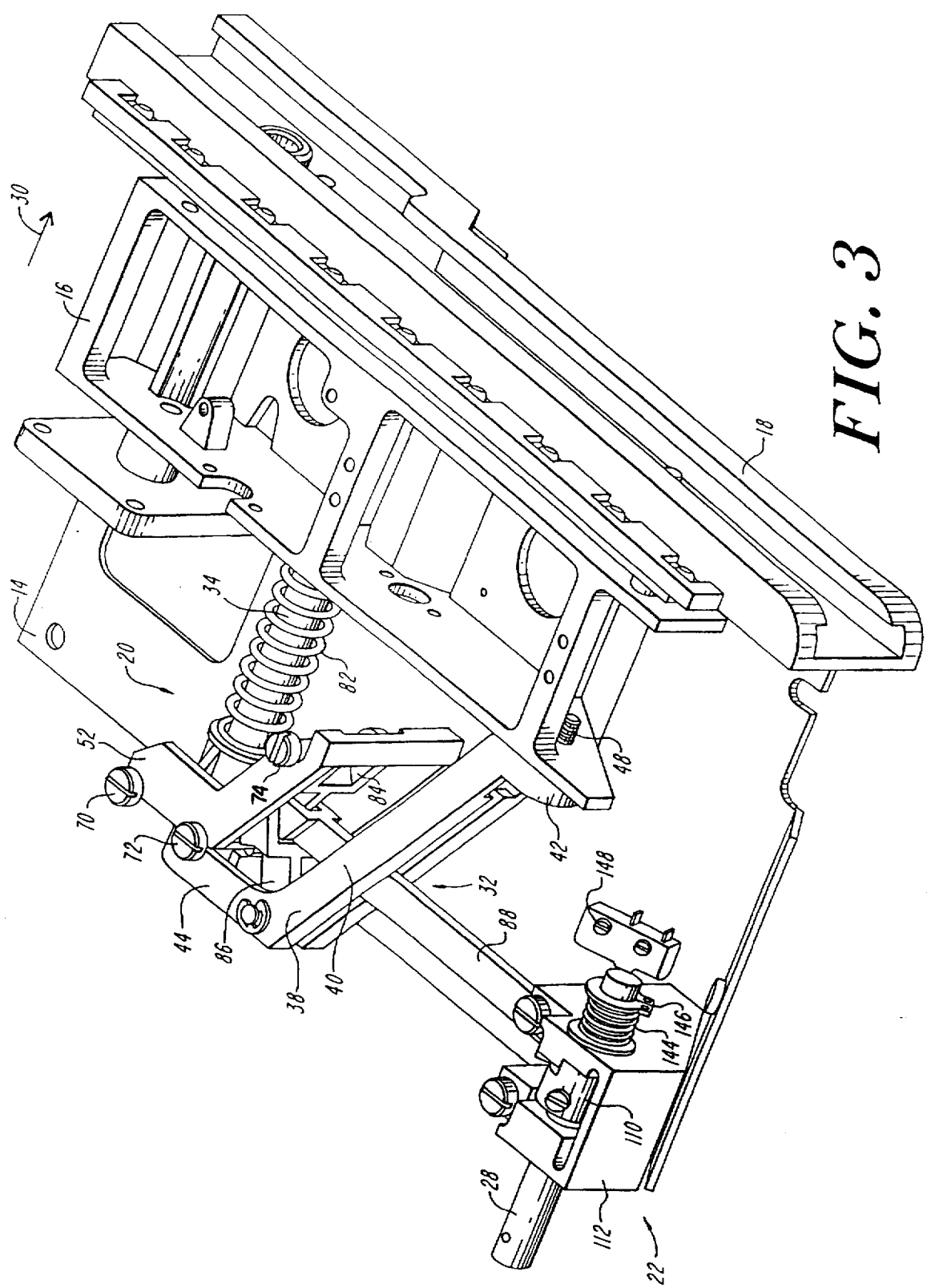
FIG. 3 is an isometric view of the retraction mechanism of FIG. 1 in the engaged position.
Figure 4:
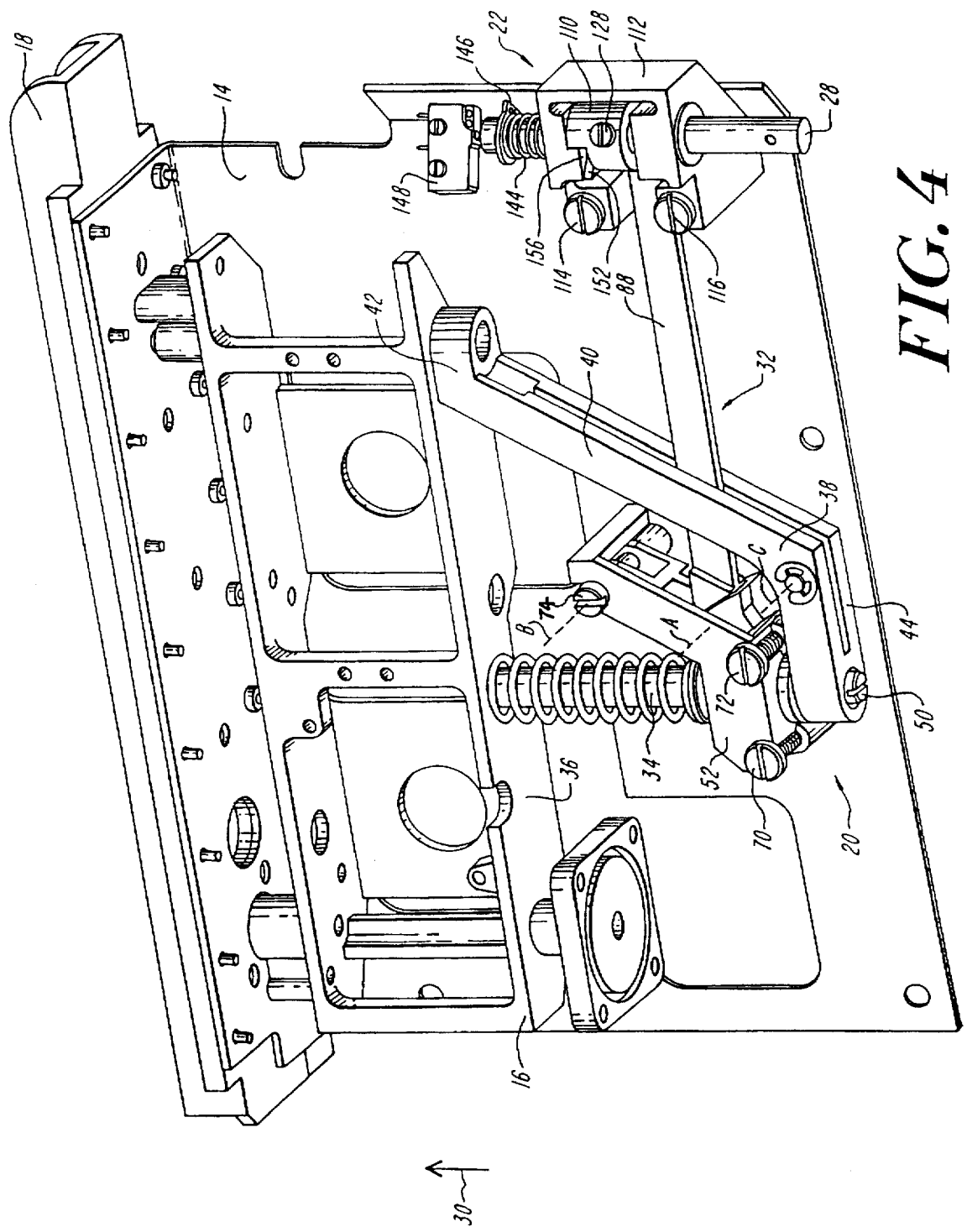
FIG. 4 is a further isometric view of the retraction mechanism of FIG. 3.
Figure 5:
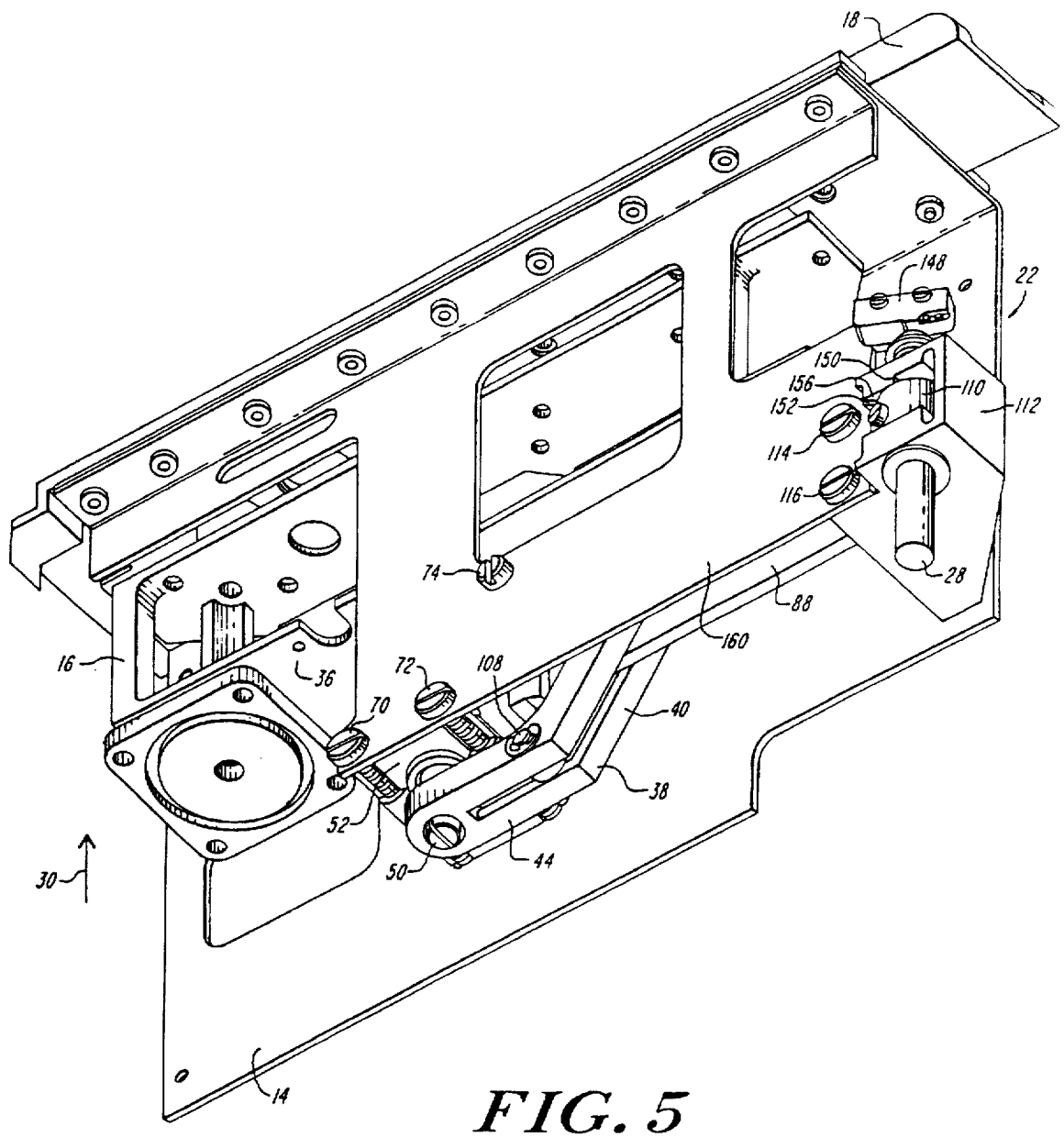
FIG. 5 is a further isometric view of the retraction mechanism of FIG. 1.

In the retracted position, the two toggle links 84,86 are aligned along a straight line defined by alignment of the axes A, B, and C on a line in a plane perpendicular to the axes, as shown in FIGS. 1, 2, 5, 7, and 8. The straight line alignment also aids in maintaining the retraction mechanism 10 in the retracted position. Referring to FIGS. 3 and 4, to engage the pumping mechanism assembly with a cassette, the connecting link 88 is pushed toward the pull rod 34 (described further below). This causes the toggle links 84,86 to rotate about the axis A. The axis A moves toward the pull rod 34. The first toggle link 84 rotates about the axis B, and the second toggle link 86 rotates about the axis C. Also, the axis C moves toward the holster 18, drawing the support arm 38 in a direction toward the holster 18 as well, indicated by the arrow 30. The support arm 38, being connected to the pull rod 34, causes the pull rod to move in a parallel direction toward the holster 18. In this manner, the pumping mechanism assembly support 16, connected to the pull rod 34, is caused to move in the direction of the arrow 30 toward the holster 18 in which the cassette may be mounted. The pumping mechanism assembly on the pumping mechanism assembly support 16 thereby engages the cassette in the holster 18.

The connecting link 88 is attached to the retraction assembly 22. The retraction assembly includes a retraction link 110 which is mounted for rotation on the retraction shaft 28 in a retraction brace 112. The retraction brace 112 is fastened to the chassis 14 in any suitable manner, such as by screws 114,116.

Figure 11A:
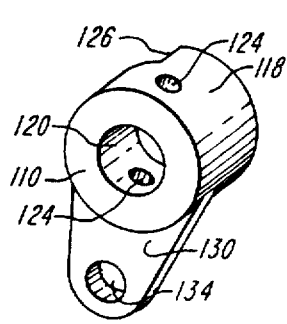
FIGS. 11A and 11B are isometric views of the retraction link of the present invention.
Figure 11B:
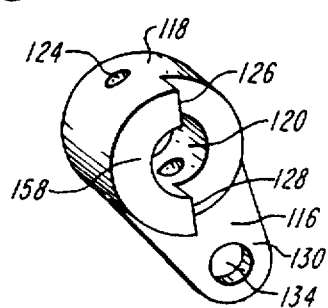

Referring to FIGS. 11A and 11B, the retraction link 110 has a cylindrical member 118 having an opening 120 therethrough sized to accommodate the retraction shaft 28. The retraction shaft may be fixed within the cylindrical member in any suitable manner, such as by providing a screw 122 through a threaded hole 124 in the cylindrical member 118 and retraction shaft 28. Accordingly, upon rotation of the retraction shaft 28, the retraction link 110 also rotates. The cylindrical member 118 of the retraction link 110 also has an upper stop 126 and a lower stop 128, discussed more particularly below, formed by a half cylinder cut-away portion, as shown more particularly in FIGS. 11A and 11B.

The retraction link 110 also has an extension 130 to which the connecting link 88 is rotatably attached in any suitable manner. For example, the connecting link may include a second forked end 132 having holes therein which align with a hole 134 in the extension. A pin or other fastener (not shown) inserted through the aligned holes thereby attaches the connecting link 88 to the retraction link 110. When the retraction link 110 is rotated about an axis defined by the retraction shaft 28, the connecting link 88 also rotates, causing the connecting link 88 to translate in a direction orthogonal to the retraction shaft axis.

Figure 12:
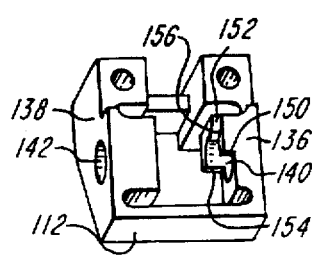
FIG. 12 is an isometric view of the retraction brace of the present invention.

The retraction shaft 28 and retraction link 110 are mounted within the retraction brace 112. The retraction brace has a pair of opposed walls 136,138, as shown in FIG. 12. Aligned openings 140,142 to accommodate the retraction shaft are formed in the opposed walls. A compression spring 144 around the retraction shaft 28 is provided between an outer surface of one 136 of the opposed walls and a clip 146 fastened to the retraction shaft 28. The spring 144 biases the shaft 28 in the direction of arrow 30 toward the holster 18, thereby tending to retain the retraction mechanism 10 in the engaged position (shown in FIGS. 3 and 4). A switch 148 is located at the end of the retraction shaft 28, in contact therewith when the retraction shaft is in the engaged position. When the retraction shaft 28 is pulled against the biassing force to retract the mechanism, discussed further below, contact with the switch 148 is broken, causing a signal that the pumping mechanism assembly is retracted to be communicated to, for example, a system controller (not shown). Other suitable biassing mechanisms and switch assemblies may be used.

The retraction link 110 fits in the space between the opposed walls 136,138 of the retraction brace 112. As shown more particularly in FIG. 12, one 136 of the opposed walls includes three shoulders formed therein to provide stops: an engaged position stop 150, a retracted position stop 152, and an overrotation stop 154.

The engaged position stop 150 is oriented to abut the upper stop 126 of the retraction link 110 in the engaged position. The engaged position stop 150 is offset from the retracted position stop 152 along a line parallel to the axis of the retraction shaft 28. Accordingly, the retraction shaft 28 must be pulled against the force of the biassing spring 144 to move the stops 126,150 out of abutment. Once the upper stop 126 and the engaged stop 150 are no longer abutting, the retraction shaft 28 can be rotated.

The retracted position stop 152 lies in a plane parallel to the axis of the retraction shaft 28. Upon rotation of the shaft, counterclockwise in FIGS. 1, 4, and 5, the upper stop 126 of the retraction link 110 abuts against the stop 152. The stop 152 is oriented at an angle chosen to prevent rotation of the retraction shaft 28 beyond the position at which the pump mechanism engages the cassette. An interior face 156 of the wall 136 of the brace 112, adjacent to and oriented orthogonally to the retracted position stop 152, abuts against the outer half-cylinder end surface 158 (FIG. 11B) to aid in retaining the shaft 28 against the biassing force of the spring 144 to lock the shaft in the rotated position. To return to the engaged position, the shaft 28 is rotated in the opposite direction, clockwise in FIGS. 1, 4, and 5, until the upper stop 126 passes the interior face 156 of the brace 112. Once past the interior face 156, the biassing force provided by the spring 144 pulls the retraction shaft 28 back into the engaged position with the upper stop 126 abutting the engaged position stop 150. In this manner, the retraction mechanism 10 tends to remain in the engaged position, thereby minimizing the likelihood of free flow of fluid on the flow path.

The overrotation stop 154 also lies in a plane parallel to the axis of the retraction shaft 28. Upon rotation of the shaft 28 back to the engaged position, the lower stop 128 of the retraction link 110 abuts against the overrotation stop 154. The overrotation stop 154 is oriented at an angle to prevent the rotation of the retraction shaft 28 beyond the position at which it is necessary to engage the pumping mechanism assembly with the cassette. Accordingly, the overrotation stop 154 further ensures that the retraction shaft 28 returns to the engaged position. It will be appreciated that other suitable locking mechanisms to retain the retraction assembly in the engaged position or the retracted position or to prevent overrotation may be provided.

The retraction mechanism 10 is relatively compact and takes up a minimal amount of space inside the infusion system housing 26. The mechanism can be held in place by a top strap 160 (FIG. 5) fastened with the three screws 70,72,74 through the pull rod brace 52 and the two screws 114,116 through the retraction brace 112. If desired, one of the screws can be an adjustable screw, incorporating some play to accommodate any adjustments needed, for example, because of variations in parts between molding lots.

The handle 24 is attached in any suitable manner to the retraction shaft 28. The handle extends outside of the housing 26 of the infusion system, opposite the side in which the cassette is mounted, to be accessible to a user. Suitable markings indicating the engaged, or cassette locked, position and the retracted, or cassette unlocked, position may be provided on the housing 26 to direct the user in the correct rotation of the handle.

The handle 24 may be formed in any suitable shape, such as a narrow wedge, and oriented to point generally upwardly in the engaged position. To retract the pumping mechanism assembly and disengage the cassette, a user pulls out on the handle, away from the cassette, and rotates the handle in a counterclockwise direction, or "downward," as indicated on FIGS. 1, 4, and 5. This orientation and motion is more intuitive for the user. Also, the first pulling step ensures that the handle will not be accidentally rotated into the retracted position, to prevent unintended free flow of fluids through the cassette.

The retraction mechanism has been described in relation to a pumping system incorporating a flow path and pumping and valve chambers on a cassette. However, the mechanism is applicable to other types of infusion systems in which the described rotary to linear motion can be employed to engage and retract a mechanism. For example, the mechanism can be used to engage and retract the pumping mechanism of a peristaltic pump. Similarly, the mechanism is not limited to systems which employ cassettes or other removable or disposable devices. The invention is not to be limited by what has been particularly shown and described, except as indicated by the appended claims.

I claim:

1. A retraction mechanism for an infusion system having a pump mechanism and a pumping mechanism assembly support, comprising:

a chassis;

a pull rod assembly comprising:

a pull rod brace fixed to said chassis, and a linearly movable assembly fixable to the pumping mechanism assembly support and linearly movably coupled to said pull rod brace for linear movement in a direction, whereby the pumping mechanism assembly support is movable with said linearly movable assembly in said direction;

a toggle linkage comprising:

a connecting link, a first toggle link, and a second toggle link, said connecting link and said first and second toggle links being rotatably coupled at first ends thereof to define a first rotation axis through said first ends of said connecting link, said first toggle link, and said second toggle link, an opposite end of said first toggle link being rotatably coupled to said chassis to define a second rotation axis, and an opposite end of said second toggle link being rotatably coupled to said linearly movable assembly to define a third rotation axis, whereby said third rotation axis is linearly movable in said direction; and a retraction assembly comprising:

a retraction brace fixed to said chassis, a retraction rod linearly movably and rotatably coupled to said retraction brace for linear motion and rotation about a fourth axis parallel to said direction, and a retraction link fixedly coupled to said retraction rod for rotation with said rod, an opposite end of said connecting link being coupled to said retraction link;

whereby rotation of said retraction link provides translational motion of said connecting link, and the translation of said connecting link provides rotation of said first and second toggle links about said first, second, and third axes and linear motion of said third axis, and the linear motion of said third axis provides linear motion of said linearly movable assembly in said direction.

2. The retraction mechanism of claim 1, wherein said linearly movable assembly further comprises:

an opening in said pull rod brace; and a pull rod disposed for linear motion in said direction in said opening.

3. The retraction mechanism of claim 2, wherein said opening is lined with a bearing material.

4. The retraction mechanism of claim 1 wherein said linearly movable assembly further comprises a support arm fixable to the pumping mechanism assembly support.

5. The retraction mechanism of claim 4, wherein said opposite end of said second toggle link is rotatably coupled to said support arm to define said third rotation axis.

6. The retraction mechanism of claim 1, wherein said first, second, and third rotation axes are oriented to be aligned along a line in a plane parallel to said direction when said retraction mechanism is in a retracted position.

7. The retraction mechanism of claim 1, wherein said pull rod assembly further comprises a biassing member fixable between said pull rod brace and the pumping mechanism assembly support, whereby the pumping mechanism assembly support is biassable in said direction.

8. The retraction mechanism of claim 1, wherein said opposite end of said second toggle link is rotatably coupled to said pull rod brace to define said third rotation axis.

9. The retraction mechanism of claim 1, further comprising a retracted position stop on said retraction brace and a corresponding retracted position stop on said retraction link positioned to abut said retraction brace retracted position stop in a retracted position.

10. The retraction mechanism of claim 1, further comprising an engaged position stop on said retraction brace and a corresponding engaged position stop on said retraction link positioned to abut said retraction brace engaged position stop in an engaged position.

11. The retraction mechanism of claim 1, further comprising:

an engaged position stop on said retraction brace and a corresponding engaged position stop on said retraction link positioned to abut said retraction brace engaged position stop in an engaged position to prevent rotation of said retraction rod about said fourth axis; and a retracted position stop on said retraction brace, offset from said retraction brace engaged position stop, and a corresponding retracted position stop on said retraction link positioned to abut said retraction brace retracted position stop in a retracted position to prevent rotation of said retraction rod about said fourth axis.

12. The retraction mechanism of claim 11, further comprising an overrotation stop on said retraction brace and a corresponding overrotation stop on said retraction link positioned to abut said retraction brace overrotation stop in the engaged position to prevent rotation of Said retraction rod beyond the engaged position.

13. The retraction mechanism of claim 1, further comprising a biassing member coupled to said retraction rod to bias said retraction rod in said direction.

14. The retraction mechanism of claim 13, further comprising a switch to detect a linear position of said retraction rod.

15. The retraction mechanism of claim 1, further comprising a handle coupled to said retraction rod.

16. A retraction mechanism for an infusion system having a chassis, a pumping mechanism assembly mounted to a pumping mechanism assembly support, and a flow path therethrough, to move the pumping mechanism assembly into an engaged position in engagement with the flow path and into a retracted position out of engagement with the flow path, said retraction mechanism comprising:

a linearly movable assembly fixable to the pumping mechanism assembly support and linearly movable coupled to the chassis for linear movement in a first direction and an opposite direction, whereby the pumping mechanism assembly support is movable with said linearly movable assembly in said first direction into the engaged position and in said opposite direction into the retracted position;

a toggle linkage comprising:

a connecting link, a first toggle link, and a second toggle link, said connecting link and said first and second toggle links being rotatably coupled at first ends thereof to define a first rotation axis through said first ends of said connecting link, said first toggle link, and said second toggle link, an opposite end of said first toggle link being rotatably coupled to the chassis to define a second rotation axis, and an opposite end of said second toggle link being rotatably coupled to said linearly movable assembly to define a third rotation axis, whereby said third rotation axis is linearly movable in said first and opposite directions; and a retraction assembly linearly movably and rotatably coupled to the chassis for linear motion and rotation about a fourth axis parallel to said first and opposite directions, an opposite end of said connecting link being coupled to said retraction assembly at a point radially spaced from said fourth axis for movement radially about said fourth axis;

whereby rotation of said retraction assembly provides translational motion of said connecting link, and the translation of said connecting link provides rotation of said first and second toggle links about said first, second, and third axes and linear motion of said third axis, and the linear motion of said third axis provides linear motion of said linearly movable assembly in said first and opposite directions.

17. The retraction mechanism of claim 16, wherein said opposite end of said second toggle link is rotatably coupled to said support arm to define said third rotation axis.

18. The retraction mechanism of claim 16, further comprising a biassing member coupled to said linearly movable member and disposed to bias the pumping mechanism assembly support in said first direction.

19. The retraction mechanism of claim 16, further comprising a bearing surface coupled to said chassis, said bearing surfacing bearing said linearly movable assembly.

20. The retraction mechanism of claim 19, wherein said bearing surface is cylindrical and said linearly movable assembly comprises a rod journaled for translational motion in said bearing surface.

21. The retraction mechanism of claim 20, wherein said linearly movable assembly further comprises a support arm fixable to the pumping mechanism assembly support.

22. The retraction mechanism of claim 16, further comprising a switch coupled to said retraction assembly to detect a position of said retraction assembly.

23. The retraction mechanism of claim 16, further comprising a handle coupled to said retraction assembly.

24. The retraction mechanism of claim 16, wherein said first, second, and third rotation axes are oriented to be aligned along a line in a plane parallel to said first and opposite directions when said retraction mechanism in the retracted position.

25. The retraction mechanism of claim 16, wherein said retraction assembly further comprises an engaged position lock assembly disposed to retain said retraction assembly in the engaged position.

26. The retraction mechanism of claim 16, wherein said retraction assembly further comprises a retracted position lock assembly disposed to retain said retraction assembly in the retracted position.

27. The retraction mechanism of claim 16, wherein said retraction assembly further comprises a biassing member disposed to retain said retraction assembly in the engaged position.

28. A retraction mechanism for an infusion system having a pump mechanism and a pumping mechanism assembly support, comprising:
　a chassis;
　a pull rod assembly comprising:
　　a pull rod brace fixed to said chassis, and
　　a linearly movable assembly comprising a support arm having a slot therethrough, said support arm fixable to the pumping mechanism assembly support and coupled to said pull rod brace for linear movement in a direction, whereby the pumping mechanism assembly support is movable with said linearly movable assembly in said direction;
　a toggle linkage comprising:
　　a connecting link, a first toggle link, and a second toggle link, said connecting link and said first and second toggle links being rotatably coupled at first ends thereof to define a first rotation axis,
　　an opposite end of said first toggle link being rotatably coupled to said chassis to define a second rotation axis,
　　an opposite end of said second toggle link being rotatably coupled to said linearly movable assembly to define a third rotation axis, whereby said third rotation axis is linearly movable in said direction, and
　　said connecting link being disposed through said slot of said support arm; and
　a retraction assembly comprising:
　　retraction brace fixed to said chassis,
　　a retraction rod coupled to said retraction brace for linear motion and rotation about a fourth axis parallel to said direction, and
　　a retraction link fixedly coupled to said retraction rod for rotation with said rod, an opposite end of said connecting link being coupled to said retraction link;
　whereby rotation of said retraction link provides translational motion of said connecting link, and the translation of said connecting link provides rotation of said first and second toggle links about said first, second, and third axes and linear motion of said third axis, and the linear motion of said third axis provides linear motion of said linearly movable assembly in said direction.

29. A retraction mechanism for an infusion system having a pump mechanism and a pumping mechanism assembly support, comprising:
　a chassis;
　a pull rod assembly comprising:
　　a pull rod brace fixed to said chassis, and
　　a linearly movable assembly fixable to the pumping mechanism assembly support and coupled to said pull rod brace for linear movement in a direction, whereby the pumping mechanism assembly support is movable with said linearly movable assembly in said direction;
　a toggle linkage comprising:
　　a connecting link, a first toggle link, and a second toggle link, said connecting link and said first and second toggle links being rotatably coupled at first ends thereof to define a first rotation axis,
　　an opposite end of said first toggle link being rotatably coupled to said chassis to define a second rotation axis, and
　　an opposite end of said second toggle link being rotatably coupled to said linearly movable assembly to define a third rotation axis, whereby said third rotation axis is linearly movable in said direction; and a retraction assembly comprising:
　　a retraction brace fixed to said chassis,
　　a retraction rod coupled to said retraction brace for linear motion and rotation about a fourth axis parallel to said direction,
　　a retraction link fixedly coupled to said retraction rod for rotation with said rod, an opposite end of said connecting link being coupled to said retraction link,
　　an engaged position stop on said retraction brace and a corresponding engaged position stop on said retraction link positioned to abut said retraction brace engaged position stop in an engaged position to prevent rotation of said retraction rod about said fourth axis, a retracted position stop on said retraction brace, offset from said retraction brace engaged position stop, and a corresponding retracted position stop on said retraction link positioned to abut said retraction brace retracted position stop in a retracted position to prevent rotation of said retraction rod about said fourth axis, and a face adjacent and orthogonal to said retraction brace retracted position stop, and a corresponding surface on said retraction link positioned to abut said face in the retracted position to prevent linear motion of said retraction rod in said direction;

whereby rotation of said retraction link provides translational motion of said connecting link, and the translation of said connecting link provides rotation of said first and second toggle links about said first, second, and third axes and linear motion of said third axis, and the linear motion of said third axis provides linear motion of said linearly movable assembly in said direction.

* * * * *

UNITED STATES PATENT AND TRADEMARK OFFICE
CERTIFICATE OF CORRECTION

PATENT NO. : 5,673,588
DATED : October 7, 1997
INVENTOR(S) : Raymond

It is certified that error appears in the above-indentified patent and that said Letters Patent is hereby corrected as shown below:

Column 8, line 25, change "Said" to --said--.

Signed and Sealed this

Twelfth Day of May, 1998

*Attest:*

BRUCE LEHMAN

*Attesting Officer*              *Commissioner of Patents and Trademarks*